United States Patent
Blagg

(10) Patent No.: US 6,579,982 B1
(45) Date of Patent: Jun. 17, 2003

(54) PYRIMIDINE-2,4,6-TRIONE METALLOPROTEINASE INHIBITORS

(75) Inventor: Julian Blagg, Canterbury (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/635,156

(22) Filed: Aug. 9, 2000

Related U.S. Application Data

(60) Provisional application No. 60/148,547, filed on Aug. 12, 1999.

(51) Int. Cl.[7] .............................................. C07D 239/60
(52) U.S. Cl. ...................... 544/300; 544/299; 544/301; 544/302; 544/295; 544/296; 544/264; 544/182; 544/68; 544/66; 544/8; 544/53; 544/58.1; 544/58.2; 544/58.6; 544/72; 544/82; 544/83; 544/96; 544/120; 544/121; 544/122; 544/123
(58) Field of Search ................... 544/298, 299, 544/300, 301, 302, 295, 296, 96, 82, 98, 60, 66, 68, 58.2, 120, 123, 122, 88, 53, 58.6, 8, 182, 264, 58.1, 72, 83, 121

(56) References Cited

FOREIGN PATENT DOCUMENTS

WO  9858925  12/1998

OTHER PUBLICATIONS

Fenner, Helmut; Grauert, Rolf W.; Hemmerich, Peter; *Justus Liebigs Ann. Chem.* (1978), (2), 193–213 (Chemical Abstract 89:109344);.

Clark–Lewis, John.; Moody, K.; *Aust. J. Chem.* (1970), 23 (6), 1229–48 (Chemical Abstract 73:35321); and.

Hafez, Ali A. Abdel; Geies, Ahmed A.; Hozien, A. Khalil, Zarif H.; *Collect. Czech. Chem. Commun.* (1994), 5 (4), 957–77 (Chemical Abstract 121:108644).

*Primary Examiner*—John M. Ford
(74) *Attorney, Agent, or Firm*—Peter C. Richardson; Paul H. Ginsburg; Krishna G. Banerjee

(57) ABSTRACT

The present invention relates to pyrimidine-2,4,6-trione metalloproteinase inhibitors of the formula

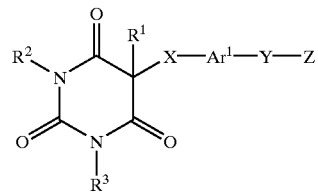

wherein X, Y, $Ar^1$, Z, $R^1$, $R^2$ and $R^3$ are as defined in the specification, and to pharmaceutical compositions and methods of treating inflammation, cancer and other disorders.

34 Claims, No Drawings

PYRIMIDINE-2,4,6-TRIONE METALLOPROTEINASE INHIBITORS

This is a U.S. Patent Non-Provisional Application which claims priority to co-pending U.S. Provisional Application No. 60/148,547 filed Aug. 12, 1999.

BACKGROUND OF THE INVENTION

The present invention relates to pyrimidine-2,4,6-trione metalloproteinase inhibitors, and to pharmaceutical compositions and methods of treatment of inflammation, cancer and other disorders.

The compounds of the present invention are inhibitors of zinc metalloendopeptidases, especially those belonging to the matrix metalloproteinase (also called MMP or matrixin) and reprolysin (also known as adamylsin) subfamilies of the metzincins (Rawlings, et al., *Methods in Enzymology*, 248, 183–228 (1995) and Stocker, et al., *Protein Science*, 4, 823–840 (1995)).

The MMP subfamily of enzymes, currently contains seventeen members (MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20). The MMP's are most well known for their role in regulating the turn-over of extracellular matrix proteins and as such play important roles in normal physiological processes such as reproduction, development and differentiation. In addition, the MMP's are expressed in many pathological situations in which abnormal connective tissue turnover is occurring. For example, MMP-13 an enzyme with potent activity at degrading type II collagen (the principal collagen in cartilage), has been demonstrated to be overexpressed in osteoarthritic cartilage (Mitchell, et al., *J. Clin. Invest.*, 97, 761 (1996)). Other MMPs (MMP-2, MMP-3, MMP-8, MMP-9, MMP-12) are also overexpressed in osteoarthritic cartilage and inhibition of some or all of these MMP's is expected to slow or block the accelerated loss of cartilage typical of joint diseases such as osteoarthritis or rheumatoid arthritis.

The mammalian reprolysins are known as ADAMs (A Disintegrin And Metalloproteinase) (Wolfberg, et al., *J. Cell Biol.*, 131, 275–278 (1995)) and contain a disintegrin domain in addition to a metalloproteinase-like domain. To date twenty-three distinct ADAMs have been identified.

ADAM-17, also known as tumor necrosis factor-alpha converting enzyme (TACE), is the most well known ADAM. ADAM-17 (TACE) is responsible for cleavage of cell bound tumor necrosis factor-alpha (TNF-$\alpha$, also known as cachectin). TNF-$\alpha$ is recognized to be involved in many infectious and autoimmune diseases (W. Friers, *FEBS Letters*, 285, 199 (1991)). Furthermore, it has been shown that TNF-$\alpha$ is the prime mediator of the inflammatory response seen in sepsis and septic shock (Spooner, et al., *Clinical Immunology and Immunopathology*, 62 S11 (1992)). There are two forms of TNF-$\alpha$, a type II membrane protein of relative molecular mass 26,000 (26 kD) and a soluble 17 kD form generated from the cell bound protein by specific proteolytic cleavage. The soluble 17 kD form of TNF-$\alpha$ is released by the cell and is associated with the deleterious effects of TNF-$\alpha$. This form of TNF-$\alpha$ is also capable of acting at sites distant from the site of synthesis. Thus, inhibitors of TACE prevent the formation of soluble TNF-$\alpha$ and prevent the deleterious effects of the soluble factor.

Select compounds of the invention are potent inhibitors of aggrecanase, an enzyme important in the degradation of cartilage aggrecan. Aggrecanase is also believed to be an ADAM (Tortorella et al., *Science*, 284, 1664 (1999)). The loss of aggrecan from the cartilage matrix is an important factor in the progression of joint diseases such as osteoarthritis and rheumatoid arthritis and inhibition of aggrecanase is expected to slow or block the loss of cartilage in these diseases.

Other ADAMs that have shown expression in pathological situations include ADAM TS-1 (Kuno, et al., *J. Biol. Chem.*, 272, 556–562 (1997)), and ADAM's 10, 12 and 15 (Wu, et al., *Biochem. Biophys. Res. Comm.*, 235, 437–442, (1997)). As knowledge of the expression, physiological substrates and disease association of the ADAM's increases the full significance of the role of inhibition of this class of enzymes will be appreciated.

It is recognized that different combinations of MMP's and ADAM's are expressed in different pathological situations. As such, inhibitors with specific selectivities for individual ADAM's and/or MMP's may be preferred for individual diseases. For example, rheumatoid arthritis is an inflammatory joint disease characterized by excessive TNF levels and the loss of joint matrix constituents. In this case, a compound that inhibits TACE and aggrecanase as well as MMP's such as MMP-13 may be the preferred therapy. In contrast, in a less inflammatory joint disease such as osteoarthritis, compounds that inhibit matrix degrading MMP's such as MMP-13 but not TACE may be preferred.

The present inventors have also discovered that it is possible to identify inhibitors of formula I with differential metalloprotease and reprolysin activity (preferably MMP-13 inhibitory activity). One group of preferred inhibitors of formula I the inventors have been able to identify include those which selectively inhibit MMP-13 preferentially over MMP-1.

Matrix metalloproteinase and reprolysin inhibitors are well known in the literature. Specifically, PCT publication WO 98/58925, published Dec. 30, 1998, refers to certain pyrimidine-2,4,6 trione MMP inhibitors. European Patent Publication 606,046, published Jul. 13, 1994, refers to certain heterocyclic MMP inhibitors. U.S. Pat. No. 5,861, 510, issued Jan. 19, 1999, refers to cyclic arylsulfonylamino hydroxamic acids that are useful as MMP inhibitors. PCT Publication WO 98/34918, published Aug. 13, 1998, refers to heterocyclic hydroxamic acids including certain dialkyl-substituted compounds that are useful as MMP inhibitors. PCT publications WO 96/27583 and WO 98/07697, published Mar. 7, 1996 and Feb. 26, 1998, respectively, refer to arylsulfonyl hydroxamic acids. PCT publication WO 98/03516, published Jan. 29, 1998 refers to phosphinates with MMP activity. PCT publication 98/33768, published Aug. 6, 1998, refers to N-unsubstituted arylsulfonylamino hydroxamic acids. PCT Publication WO 98/08825 and WO 98 08815, both published Mar. 5, 1998, refer to certain heterocyclic MMP inhibitors. U.S. patent application Ser. Nos. 60/096232 and 60/096256 both filed Aug. 12, 1998 also refer to heterocyclic hydroxamic acid MMP and TACE inhibitors. Each of the above referenced publications and applications is hereby incorporated by reference in its entirety.

SUMMARY OF THE INVENTION

The present invention relates to compounds of the formula:

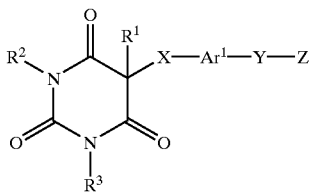

wherein $R^1$ is hydrogen, $(C_1-C_4)$perfluoroalkyl, $(C_1-C_8)$ alkyl or $(C_3-C_8)$cycloalkyl, wherein said $(C_1-C_8)$alkyl or $(C_3-C_8)$cycloalkyl may optionally contain one to three heteroatoms independently selected from oxygen, $>NR^5$ and sulfur; wherein said $(C_1-C_8)$alkyl or $(C_3-C_8)$ cycloalkyl may also optionally be substituted by one to two substituents independently selected from $(C_1-C_4)$ alkyl, $(C_6-C_{10})$aryl, $(C_2-C_{10})$heteroaryl, OH, $NH_2$, $(C_1-C_4)$alkylamino, di[$(C_1-C_4)$alkyl]amino, $(C_3-C_8)$ cycloalkylamino, $(C_3-C_8)$cycloalkyl$(C_1-C_4)$ alkylamino, $(C_1-C_4)$alkoxy, —$CONH_2$, —$CONHR^4$, —$CON(R^4)_2$ and $(C_3-C_8)$cycloalkyl, wherein said $(C_3-C_8)$cycloalkyl may optionally contain one or two heteroatoms independently selected from $>NR^5$, oxygen and sulfur.

$R^2$ and $R^3$ are independently selected from hydrogen or $(C_1-C_4)$alkyl wherein said $(C_1-C_4)$alkyl may optionally contain one heteroatom selected from oxygen, $>NR^5$ or sulfur and said $(C_1-C_4)$alkyl may be optionally substituted by $(C_6-C_{10})$aryl, $(C_2-C_{10})$heteroaryl, OH, $NH_2$, $(C_1-C_4)$alkylamino, di[$(C_1-C_4)$alkyl]amino, $(C_3-C_8)$cycloalkylamino, $(C_3-C_8)$cycloalkyl$(C_1-C_4)$ alkylamino, $(C_1-C_4)$alkoxy, —$CON(R^4)_2$ or $(C_3-C_8)$ cycloalkyl; wherein said $(C_3-C_8)$cycloalkyl may contain one or two heteroatoms independently selected from $>NR^5$, oxygen and sulfur;

X is selected from the group consisting of oxygen, sulfur, $>SO_2$, $>S=O$, $>NR^4$, —$CH_2O$—, —$OCH_2$—, —$CH_2S$—, —$CH_2(S=O)$—, —$CH_2SO_2$—, —$SCH_2$—, —$SOCH_2$—, —$SO_2CH_2$—, —$N(R^4)$ $CH_2$—, —$CH_2N(R^4)$—, —$N(R^4)SO_2$— and —$SO_2N$ $(R^4)$—;

$R^4$ wherever it occurs is independently selected from hydrogen and $(C_1-C_4)$alkyl;

$R^5$ wherever it occurs is independently selected from hydrogen, $(C_1-C_4)$alkyl, $(C_6-C_{10})$aryl, $(C_2-C_{10})$ heteroaryl, OH, —$CONH_2$, —$CONHR^4$, —$CON(R^4)_2$ and $(C_3-C_8)$cycloalkyl;

Y is selected from the group consisting of a bond, oxygen, sulfur, $>SO_2$, $>S=O$, $>NH$, —$CH_2$—, —$CH_2O$—, —$OCH_2$—, —$CH_2S$—, —$CH_2(S=O)$—, —$CH_2SO_2$—, —$SCH_2$—, —$SOCH_2$—, —$SO_2CH_2$—, —$NHCH_2$—, —$CH_2NH$—, —$CH_2CH_2$—, —$CH=CH$—, —$NHSO_2$— and —$SO_2NH$—;

$Ar^1$ is $(C_6-C_{10})$aryl or $(C_2-C_{10})$heteroaryl; and

Z is $(C_6-C_{10})$aryl, $(C_3-C_8)$cycloalkyl, $(C_3-C_8)$cycloalkyl $(C_1-C_4)$alkyl or $(C_2-C_{10})$heteroaryl;

wherein one or two of the ring carbon atoms of said $(C_3-C_8)$cycloalkyl or $(C_3-C_8)$cycloalkyl$(C_1-C_4)$alkyl may optionally be replaced by heteroatoms independently selected from oxygen, sulfur and $NR^5$;

wherein $Ar^1$ and Z may be optionally substituted on any of the ring carbon atoms capable of forming an additional bond by one to three substituents independently selected from F, Cl, Br, CN, OH, $(C_1-C_4)$alkyl, $(C_1-C_4)$perfluoroalkyl, $(C_1-C_4)$perfuoroalkoxy, $(C_1-C_4)$alkoxy, and $(C_3-C_8)$cycloalkyloxy;

or the pharmaceutically acceptable salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The term "a bond", as used herein in the group Y, means that the groups $Ar^1$ and Z are directly connected through a carbon-carbon bond so as to form pendent aryl rings such as diphenyl.

The term "alkyl", as used herein, unless otherwise indicated, includes saturated monovalent hydrocarbon radicals having straight, branched or cyclic moieties or combinations thereof. Alkyl groups, wherever they occur, may be optionally substituted by a suitable substituent.

The term "alkenyl", as used herein, unless otherwise indicated, includes hydrocarbon radicals containing at least one olefin linkage and having straight, branched or cyclic moieties or combinations thereof.

The term "alkynyl", as used herein, unless otherwise indicated, includes hydrocarbon radicals containing at least one carbon-carbon triple bond linkage and having straight, branched or cyclic moieties or combinations thereof.

The term "alkoxy", as used herein, includes O-alkyl groups wherein "alkyl" is as defined above.

The term "halo", as used herein, unless otherwise indicated, includes fluorine, chlorine, bromine or iodine, preferably fluorine or chlorine.

The term "aryl", as used herein, unless otherwise indicated, includes an organic radical derived from an aromatic hydrocarbon by removal of one or more hydrogens, such as phenyl or naphthyl, optionally substituted by 1 to 3 suitable substituents such as fluoro, chloro, cyano, nitro, trifluoromethyl, $(C_1-C_6)$alkoxy, $(C_6-C_{10})$aryloxy, $(C_3-C_8)$ cycloalkyloxy, trifluoromethoxy, difluoromethoxy, or $(C_1-C_6)$alkyl.

The term "heteroaryl", as used herein, unless otherwise indicated, includes an organic radical derived from an aromatic heterocyclic compound by removal of one or more hydrogens, such as pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 3 suitable substituents as defined below such as fluoro, chloro, trifluoromethyl, $(C_1–C_6)$alkoxy, $(C_6–C_{10})$aryloxy, $(C_3–C_8)$ cycloalkyloxy, trifluoromethoxy, difluoromethoxy or $(C_1–C_6)$alkyl.

"A suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, carboxy groups, amino groups, alkyl— and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, an arylsulfonyl groups and the like.

Some compounds of formula I contain chiral centers and therefore exist in different enantiomeric forms. This invention relates to all optical isomers, enantiomers, diasteriomers and stereoisomers of the compounds of formula I and mixtures thereof. The compounds of the invention also exist in different tautomeric forms. This invention relates to all tautomers of formula I.

Preferred compounds of the invention are those wherein $R^2$ and $R^3$ are each hydrogen.

Other preferred compounds of the invention include those wherein X is oxygen, —OCH$_2$—, —CH$_2$O—, more preferably wherein X is oxygen; more preferably wherein Y is a bond, oxygen, sulfur, —CH$_2$—, >SO$_2$, —OCH$_2$— or —CH$_2$O—, more preferably wherein Y is oxygen, —OCH$_2$— or —CH$_2$O—, most preferably wherein Y is oxygen.

Other embodiments of the invention include those compounds of formula I wherein X is sulfur, >SO$_2$, —SCH$_2$—, —CH$_2$S—, —CH$_2$SO$_2$— or —SO$_2$CH$_2$—, more preferably wherein Y is a bond, oxygen, sulfur, —CH$_2$—, >SO$_2$, —OCH$_2$— or —CH$_2$O—, more preferably wherein Y is oxygen, —OCH$_2$— or —CH$_2$O—, most preferably wherein Y is oxygen.

Other embodiments of the invention include those compounds of formula I wherein X is, >NR$^4$, —CH$_2$NR$^4$—, or —R$_4$CH$_2$—, more preferably wherein Y is a bond, oxygen, sulfur, —CH$_2$—, >SO$_2$, —OCH$_2$— or —CH$_2$O—, more preferably wherein Y is oxygen, —OCH$_2$— or —CH$_2$O—, most preferably wherein Y is oxygen.

Other embodiments of the invention include those compounds of formula I wherein X is —(R$^4$)SO$_2$— or —SO$_2$N (R$^4$)—, more preferably wherein Y is a bond, oxygen, sulfur, —CH$_2$—, >SO$_2$, —OCH$_2$— or —CH$_2$O—, more preferably wherein Y is oxygen, —OCH$_2$—, most preferably wherein Y is oxygen.

Other preferred compounds are those wherein Ar$^1$ is optionally substituted phenyl.

Other embodiments of the invention include those compounds of formula I wherein Z is $(C_6–C_{10})$aryl, preferably phenyl, optionally substituted with one or more substituents, preferably zero, one or two substituents, independently selected from F, Cl, Br, —CN, OH, $(C_1–C_4)$alkyl, $(C_1–C_4)$ perfluoroalkyl, $(C_1–C_4)$perfluoroalkoxy, $(C_1–C_4)$alkoxy and $(C_3–C_8)$cycloalkyloxy.

Other embodiments of the invention include those compounds of formula I wherein Z is $(C_3–C_8)$cycloalkyl (i.e. $(C_3–C_8)$cycloalkyl or $(C_3–C_8)$cycloalkyloxy-$(C_1–C_4)$alkyl), wherein one or two of the ring carbon atoms of said $(C_3–C_8)$cycloalkyl may optionally be replaced by heteroatoms independently selected from oxygen, sulfur or NR$^5$, wherein R$^5$ is selected from hydrogen, $(C_1–C_4)$alkyl, $(C_6–C_{10})$aryl, $(C_2–C_{10})$heteroaryl, OH, —CONH$_2$, —CONHR$^4$, —CON(R$^4$)$_2$ and $(C_3–C_8)$cycloalkyl. Such preferred groups include cyclopropyl, cyclobutyl, cyclopentyl, cyclohexyl, tetrahydrofuranyl, tetrahydropyranyl, N-methyl-3-azetidinyl, piperazinyl, piperidinyl, 1,3-oxazolidin-4-on-5-yl, 1,3-oxazolidin-2,4-dion-5-yl, 4,5-dihydro-1,2-oxazolidin-3-on-4-yl, 1,3-thiazolidin-4-on-5-yl, 1,3-thiazolidin-2,4-dion-5-yl, 1,3-imidazolidin-4-on-5-yl, 1,3-imidazolin-2,4-dion-5-yl, 1,2-pyrazolidin-3-on-4-yl, tetrahydro-1,3-oxazin-4-on-5-yl, tetrahydro-1,3-oxazin-2,4-dion-5-yl, morpholinyl, morpholin-3-on-2-yl, morpholin-3,5-dion-2-yl, 2,3-dihydro-1,4-oxazin-3-on-2-yl, tetrahydro-1,3-thiazin-4-on-5-yl, tetrahydro-1,3-thiazin-2,4-dion-5-yl, thiomorpholinyl, thiomorpholin-3-on-2-yl, thiomorpholin-3,5-dion-2-yl, 2,3-dihydro-1,4-thiazin-3-on-2-yl, hexahydro-1,2-diazin-3-on-4-yl, 4,5-dihydro-2H-pyridazin-3-on-4-yl, hexahydro-1,3-diazin-2,4-dion-5-yl, piperazin-2-on-3-yl, piperazin-2,6-dion-3-yl, tetrahydro-1,3,4-thiadiazin-5-on-6-yl, 5,6-dihydro-1,3,4-thiadiazin-5-on-6-yl, 1,3,4-oxadiazin-5-on-6-yl, 5,6-dihydro-1,2,4-oxadiazin-5-on-6-yl, tetrahydro-1,2,4-oxadiazin-5-on-6-yl, 1,2,4-triazin-5-on-6-yl, tetrahydro-1,2, 4-oxadiazin-5-on-6-yl, 5,6-dihydro-1-2,4-oxadiazin-5-on-6-yl, 1,2,4-oxadiazin-3,5-dion-6-yl, and 1,2,4-6-on-5-yl, preferably cyclopropyl, cyclobutyl, cyclopentyl, cyclohexyl, tetrahydrofuranyl, tetrahydropyranyl, N-methyl-3-azetidinyl, piperazinyl, piperidinyl, N-methylpiperidinyl and morpholinyl more preferably cyclopropyl, cyclobutyl, cyclopentyl, cyclohexyl, tetrahydrofuranyl and tetrahydropyranyl, most preferably cyclopropyl, tetrahydrofuranyl and tetrahydropyranyl.

Other embodiments of the invention include those compounds of formula I wherein Z is $(C_3–C_8)$cycloalkyl$(C_1–C_4)$ alkyl; wherein one or two of the ring carbon atoms of said $(C_3–C_8)$cycloalkyl$(C_1–C_4)$alkyl may optionally be replaced by heteroatoms independently selected from oxygen, sulfur or >NR$^5$, wherein R$^5$ is selected from hydrogen, $(C_1–C_4)$ alkyl, $(C_6–C_{10})$aryl, $(C_2–C_{10})$heteroaryl, OH, —CONH$_2$, —CONHR$^4$, —CON(R$^4$)$_2$ and $(C_3–C_8)$cycloalkyl. Preferred cycloalkyl and heterocycloalkyl rings are as described above. Preferred alkyl of said $(C_3–C_8)$cycloalkyl$(C_1–C_4)$ alkyl are methylene and ethylene.

Other embodiments of the invention include those compounds of formula I wherein Z is $(C_2–C_{10})$heteroaryl; preferably pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, more preferably pyridyl, pyrimidyl or pyrazinyl, most preferably pyridyl; wherein each of said $(C_2–C_{10})$heteroaryl may optionally be substituted by 1 to 3 suitable substituents, such as fluoro, chloro, trifluoromethyl, $(C_1–C_6)$alkoxy, $(C_1–C_{10})$aryloxy, trifluoromethoxy, difluoromethoxy or $(C_1–C_6)$alkyl.

Other preferred compounds of the invention include those wherein Ar$^1$ is phenyl or $(C_2–C_{10})$heteroaryl; preferably pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, more preferably phenyl, pyridinyl, pyrazinyl, pyrimidyl, most preferably pyridyl or phenyl optionally substituted by 1 to 3 suitable substituents, such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

Other preferred compounds of the invention include those wherein $Ar^1$ and Z are substituted on any of the ring carbon atoms capable of forming an additional bond by one or more substituents independently selected from F, Cl, Br, —CN, OH, $(C_1-C_4)$alkyl, $(C_1-C_4)$perfluoroalkyl, $(C_1-C_4)$perfluoroalkoxy, $(C_1-C_4)$alkoxy and $(C_3-C_8)$cycloalkyloxy.

Most preferred compounds of the invention include compounds of formula I, wherein X is oxygen, Y is a bond, oxygen, sulfur, —CH$_2$—, >SO$_2$, —OCH$_2$— or —CH$_2$O—; $R^1$ is hydrogen or $(C_1-C_4)$alkyl; wherein said $(C_1-C_4)$alkyl may optionally contain one to two heteroatoms independently selected from oxygen and >NR$^5$, wherein said $(C_1-C_4)$alkyl chain may also optionally be substituted by one to three substituents (preferably zero, one or two substituents) independently selected from $(C_1-C_4)$alkyl, OH, NH$_2$, $(C_1-C_4)$alkylamino, di[$(C_1-C_4)$alkyl]amino, $(C_1-C_4)$alkoxy, —CONH$_2$, —CONHR$^4$ and CON(R$^4$)$_2$; and $R^2$ and $R^3$ are independently selected from hydrogen and $(C_1-C_4)$alkyl.

Other embodiments of the invention include compounds of the formula I, wherein $R^1$ is $(C_1-C_8)$alkyl optionally containing one to three heteroatoms (preferably two heteroatoms separated by at least one carbon atom preferably wherein said heteroatom is —NH— or O, most preferably O), wherein said $(C_1-C_8)$alkyl is substituted with OH, NH$_2$, $(C_1-C_4)$alkylamino, di[$(C_1-C_4)$alkyl]amino, $(C_1-C_4)$alkoxy or —CON(R$^4$)$_2$, preferably di[$(C_1-C_4)$alkyl]amino.

Other embodiments of the invention include compounds of the formula I, wherein at least one of $R^2$ or $R^3$ is $(C_1-C_4)$alkyl, optionally substituted with one heteroatom (preferably said heteroatom is —H— or —O—, most preferably —O—), wherein said $(C_1-C_4)$alkyl is substituted with one or two groups independently selected from $(C_6-C_{10})$aryl or $(C_2-C_{10})$heteroaryl.

Other preferred compounds of the invention include those wherein:

$R^1$ is methyl; $R^2$ and $R^3$ are each hydrogen; X is oxygen; Y is oxygen; and Z is $(C_6-C_{10})$aryl;

$R^1$ is n-butyl; $R^2$ and $R^3$ are each hydrogen; X is oxygen; Y is oxygen; and Z is $(C_6-C_{10})$aryl;

$R^1$ is methyl; $R^2$ and $R^3$ are each hydrogen; X is oxygen; Y is oxygen; and Z is $(C_6-C_{10})$aryl; and $R^1$ is n-butyl; $R^2$ and $R^3$ are each hydrogen; X is oxygen; Y is oxygen; and Z is $(C_6-C_{10})$aryl.

Specific preferred compounds of formula I are selected from the group consisting of:

5-Methyl-5-(4-phenoxy-phenoxy)-pyrimidine-2,4,6-trione;

5-Methyl-5-(4-(4'-fluorophenoxy)-phenoxy)-pyrimidine-2,4,6-trione;

5-n-Butyl-5-(4-phenoxy-phenoxy)-pyrimidine-2,4,6-trione;

5-n-Butyl-5-(4-(4'-fluorophenoxy)-phenoxy)-pyrimidine-2,4,6-trione;

5-Methyl-5-(4-phenyl-phenoxy)-pyrimidine-2,4,6-trione;

5-Methyl-5-(3-phenyl-phenoxy)-pyrimidine-2,4,6-trione; and

5-Methyl-5-(4-benzyloxy-phenoxy)-pyrimidine-2,4,6-trione;

or pharmaceutically acceptable salts thereof.

Other compounds of the invention include:

5-Methyl-5-(4-(4'-chlorophenoxy)-phenoxy)-pyrimidine-2,4,6-trione;

5-Methyl-5-(4-(4'-cyanophenoxy)-phenoxy)-pyrimidine-2,4,6-trione;

5-Methyl-5-(4-(4'-trifluoromethylphenoxy)-phenoxy)-pyrimidine-2,4,6-trione;

5-Methyl-5-(4-(4'-methoxyphenoxy)-phenoxy)-pyrimidine-2,4,6-trione;

5-Methyl-5-(4-(3'-chlorophenoxy)-phenoxy)-pyrimidine-2,4,6-trione;

5-Methyl-5-(4-(3'-fluorophenoxy)-phenoxy)-pyrimidine-2,4,6-trione;

5-Methyl-5-(4-(3'-trifluorophenoxy)-phenoxy)-pyrimidine-2,4,6-trione;

5-Methyl-5-(4-(4'-chlorophenylmethoxy)-phenoxy)-pyrimidine-2,4,6-trione;

5-Methyl-5-(4-(4'-fluorophenylmethoxy)-phenoxy)-pyrimidine-2,4,6-trione;

5-Methyl-5-(4-(4'-fluoro-2'-chloro-phenyl methoxy)-phenoxy)-pyrimidine-2,4,6-trione;

5-Methyl-5-(4-(4'-chloro-2'-fluoro-phenylmethoxy)-phenoxy)-pyrimidine-2,4,6-trione;

5-Methyl-5-(4-(4'-fluoro-2'-methyl-phenylmethoxy)-phenoxy)-pyrimidine-2,4,6-trione;

5-Methyl-5-(4-(4'-fluoro-2'-trifluoromethyl-phenylmethoxy)-phenoxy)-pyrimidine-2,4,6-trione;

5-Methyl-5-(4-(4'-fluoro-2'-trifluorometyl-phenyl methoxy)-phenoxy)-pyrimidine-2,4,6-trione;

5-Methyl-5-(4-(pyridin-2-yl)-phenoxy)-pyrimidine-2,4,6-trione;

5-Methyl-5-(4-(4'-fluoro-pyridin-2-yl)-phenoxy)-pyrimidine-2,4,6-trione;

5-Methyl-5-(4-(4'-chloro-pyridin-2-yl)-phenoxy)-pyrimidine-2,4,6-trione;

5-Methyl-5-(4-(pyridin-4-yl)-phenoxy)-pyrimidine-2,4,6-trione;

5-Methyl-5-(4-(pyridin-3-yl)-phenoxy)-pyrimidine-2,4,6-trione;

5-Methyl-5-(4-(pyrimidin-2-yl)-phenoxy)-pyrimidine-2,4,6-trione;

5-Methyl-5-(4-(pyrimidin-4-yl)-phenoxy)-pyrimidine-2,4,6-trione;

5-Methyl-5-(4-(pyrazin-3-yl)-phenoxy)-pyrimidine-2,4,6-trione;

5-Methyl-5-(4-(4-(pyrazin-4-yl)-phenoxy)-pyrimidine-2,4,6-trione;

1,5-Dimethyl-5-(4-(4'-fluorophenylmethoxy)-phenoxy)-pyrimidine-2,4,6-trione;

1-Ethyl, 5-Methyl-5-(4-(4'-fluorophenylmethoxy)-phenoxy)-pyrimidine-2,4,6-trione;

1-(2-methoxyethyl)-5-Methyl-5-(4-(4'-fluorophenylmethoxy)-phenoxy)-pyrimidine-2,4,6-trione;

1-(2-dimethylamino-ethyl)-5-Methyl-5-(4-(4'-fluorophenylmethoxy)-phenoxy)-pyrimidine-2,4,6-trione;

1-Cyclopropylmethyl-5-Methyl-5-(4-(4'-fluorophenylmethoxy)-phenoxy)-pyrimidine-2,4,6-trione;

5-Dimethylaminomethyl-5-(4-(4'-fluorophenylmethoxy)-phenoxy)-pyrimidine-2,4,6-trione;

5-(2-dimethylamino-ethyl)-5-(4-(4'-fluorophenylmethoxy)-phenoxy)-pyrimidine-2,4,6-trione;

5-(2-methoxyethyl)-5-(4-(4'-fluorophenylmethoxy)-phenoxy)-pyrimidine-2,4,6-trione;

5-Cyclopropymethyl-5-(4-(4'-fluorophenylmethoxy)-phenoxy)-pyrimidine-2,4,6-trione;

5-Ethyl-5-(4-(4'-fluorophenylmethoxy)-phenoxy)-pyrimidine-2,4,6-trione;

5-Trifluoromethyl-5-(4-(4'-fluorophenylmethoxy)-phenoxy)-pyrimidine-2,4,6-trione;

5-Isopropyl -5-(4-(4'-fluorophenylmethoxy)-phenoxy)-pyrimidine-2,4,6-trione;

5-lsobutyryl-5-(4-(4'-fluorophenylmethoxy)-phenoxy)-pyrimidine-2,4,6-trione;

5-Methyl-5-(4-(4'-fluorophenylmethoxy)-phenylthio)-pyrimidine-2,4,6-trione;

5-Methyl-5-(4-(4'-fluorophenylmethoxy)-phenylsulfonyl)-pyrimidine-2,4,6-trione;

5-Methyl-5-(4-(4'-fluorophenylmethoxy)-phenylsulfoxy)-pyrimidine-2,4,6-trione;

5-Methyl-5-(N-4-(4'-fluorophenylmethoxy)-phenylamino)-pyrimidine-2,4,6-trione;

5-Methyl-5-(N-Methyl-N-4-(4'-fluorophenylmethoxy)-phenyl-amino)-pyrimidine-2,4,6-trione;

5-(4-(4'-Fluorophenoxy)-phenoxy)-pyrimidine-2,4,6-trione;

5-(4-(4'-Chlorophenoxy)-phenoxy)-pyrimidine-2,4,6-trione;

5-Methyl-5-(4-(4'-fluorophenyl)-phenoxy)-pyrimidine-2,4,6-trione;

5-Methyl-5-(4-(4'-chlorophenyl)-phenoxy)-pyrimidine-2,4,6-trione;

5-Methyl-5-(3-(4'-fluorophenyl)-phenoxy)-pyrimidine-2,4,6-trione;

5-Methyl-5-(3-(4'-chlorophenyl)-phenoxy)-pyrimidine-2,4,6-trione;

5-Methyl-5-(5-(4'-fluorophenoxy)-2-pyridyloxy)-pyrimidine-2,4,6-trione;

5-Methyl-5-(3-(4'-fluorophenoxy)-pyrimidine-2,4,6-trione;

5-Methyl-5-(3-(4'-fluorophenoxy)-6-pyrazinyloxy)-pyrimidine-2,4,6-trione;

5-Methyl-5-(2-(4'-fluorophenoxy)-5-pyrimidyloxy)-pyrimidine-2,4,6-trione;

5-Methyl-5-(2-(4'-fluorophenoxy)-5-pyridyloxy)-pyrimidine-2,4,6-trione;

5-Methyl-5-(4-(cyclobutylmethoxy)-phenoxy)-pyrimidine-2,4,6-trione;

5-Methyl-5-(4-(cyclopentylmethoxy)-phenoxy)-pyrimidine-2,4,6-trione;

5-Methyl-5-(4-(3'-tetrahydrofuranylmethoxy)-phenoxy)-pyrimidine-2,4,6-trione;

5-Methyl-5-(4-(4'-tetrahydropyranylmethoxy)-phenoxy)-pyrimidine-2,4,6-trione; and 5-Methyl-5-(4-(N-methyl-3-azetidinylmethoxy)-phenoxy)-pyrimidine-2,4,6-trione;

or pharmaceutically acceptable salts thereof.

The present invention also relates to a pharmaceutical composition for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as tumor invasion, tumor growth, tumor metastasis, solid tumor cancer including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, corneal scarring, scleritis, AIDS, sepsis, septic shock and other diseases characterized by metalloproteinase activity and other diseases characterized by mammalian reprolysin activity in a mammal, including a human, comprising an amount of a compound of formula I or a pharmaceutically acceptable salt thereof effective in such treatments and a pharmaceutically acceptable carrier.

The present invention also relates to a pharmaceutical composition for the inhibition of (a) matrix metalloproteinases or other metalloproteinases involved in matrix degradation, or (b) a mammalian reprolysin (such as aggrecanase or ADAM's TS-1, 10, 12, 15 and 17, most preferably aggrecanase or ADAM-17) in a mammal, including a human, comprising an effective amount of a compound of formula I or a pharmaceutically acceptable salt thereof.

The present invention also relates to a method for treating a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer (such as tumor invasion, tumor growth, tumor metastasis, solid tumor cancer including colon cancer, breast cancer, lung cancer and prostrate cancer and hematopoietic malignancies including leukemias and lymphomas), tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neurodegenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, corneal scarring, scleritis, AIDS, sepsis, septic shock and other diseases characterized by matrix metalloproteinase activity and other diseases characterized by mammalian reprolysin activity in a mammal, including a human, comprising administering to said mammal an amount of a compound of formula I or a pharmaceutically acceptable salt thereof effective in treating such a condition.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The present invention also relates to a method for the inhibition of (a) matrix metalloproteinases or other metalloproteinases involved in matrix degradation, or (b) a mammalian reprolysin (such as aggrecanase or ADAM's TS-1, 10, 12, 15 and 17, preferably aggrecanase or ADAM-17) in a mammal, including a human, comprising administering to said mammal an effective amount of a compound of formula I or a pharmaceutically acceptable salt thereof.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{31}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in the Schemes and/or in the Examples and Preparations below, by substituting a readily available isotopically-labelled reagent for a non-isotopically-labelled reagent.

This invention also encompasses pharmaceutical compositions containing prodrugs of compounds of the formula I. This invention also encompasses methods of treating or preventing disorders that can be treated or prevented by the inhibition of matrix metalloproteinases or the inhibition of mammalian reprolysin comprising administering prodrugs of compounds of the formula I. Compounds of formula I having free amino, amido, hydroxy, sulfonamide or carboxylic groups can be converted into prodrugs. Prodrugs include compounds wherein an amino acid residue, or a polypeptide chain of two or more (e.g., two, three or four) amino acid residues which are covalently joined through peptide bonds to free amido, amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters, which are covalently, bonded to the above substituents of formula I through the carbonyl carbon prodrug sidechain.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as Remicade®) and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, paracoxib and rofecoxib, analgesics LTD-4, LTB-4 and 5-LO inhibitors, p38 kinase inhibitors and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegiline and rasagiline, comP inhibitors such as Tasmar, A-2 inhibitors, dopamine reuptake inhibitors, NMDA antagonists, Nicotine agonists, NK-1 inhibitors, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

DETAILED DESCRIPTION OF THE INVENTION

The following reaction Scheme illustrates the preparation of the compounds of the present invention. Unless otherwise indicated X, Y, Ar$^1$, Z, R$^1$, R$^2$ and R$^3$ in the reaction Schemes and the discussion that follows is defined as above.

SCHEME 1
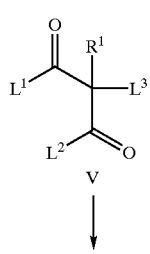
V
↓
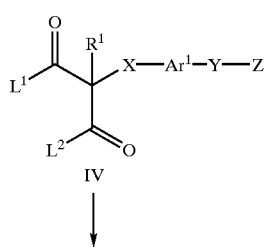
IV
↓
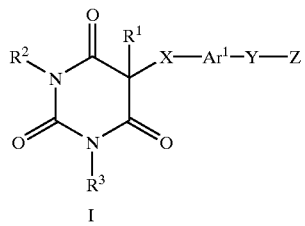
I
SCHEME 2
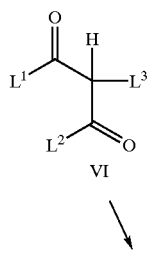  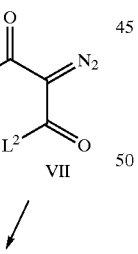
VI     VII
↓     ↓
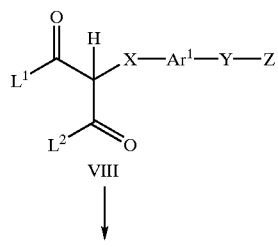
VIII
↓
-continued
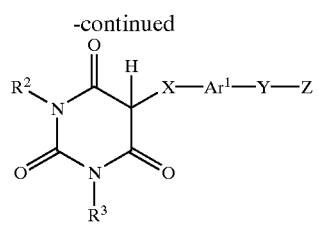
IX
↓
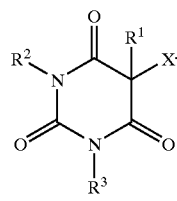
I
SCHEME 3
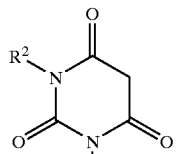
XII
↓
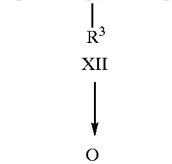
X
↓
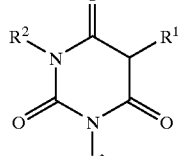
XI
↓
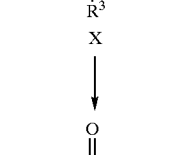
I

SCHEME 4

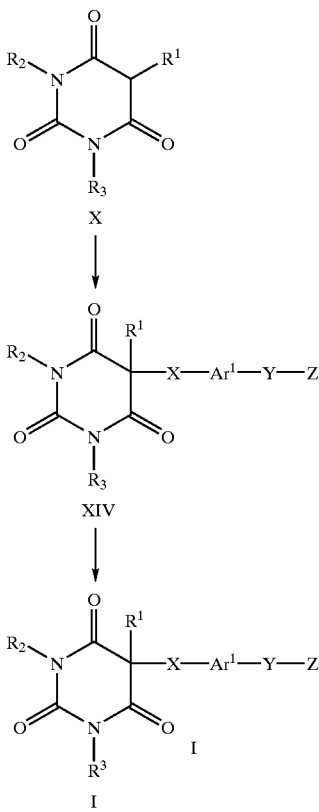

Scheme 1 refers to the preparation of compounds of the formula I in a two step synthesis from compounds of the formula V. Referring to Scheme 1, a compound of the formula I is prepared from a compound of the formula IV, wherein $L^1$ and $L^2$ are leaving groups such as methoxy, ethoxy, benzyloxy or chloro, preferably ethoxy, by reaction with a urea derivative of the formula III:

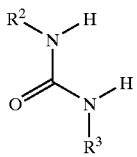   III in the presence of a strong base in a polar solvent. Suitable bases include sodium methoxide, sodium ethoxide and magnesium methoxide, preferably sodium ethoxide. Suitable solvents include alcohols (such as ethanol) or tetrahydrofuran, preferably absolute ethanol. The aforesaid reaction is conducted at a temperature of about 20° C. to about 90° C. preferably about 50° C. to about 65° C. for a time period between about 15 minutes to about 16 hours.

The compound of formula IV is prepared from a compound of formula V, wherein $L^3$ is a leaving group such as halo, p-tolylsulfonyloxy (OTs) or methylsulfonyloxy (OMs), preferably halo, most preferably chloro or bromo, by reaction with a compound of the formula HX-Ar$^1$—Y—Z in the presence of a base in a polar solvent. Suitable solvents include dimethylformamide (DMF), alcohols (such as ethanol) or tetrahydrofuran, preferably ethanol. The aforesaid reaction is conducted at a temperature of about 20° C. to about 90° C. preferably about 50° C. to about 65° C. for a time period between about 15 minutes to about 16 hours.

The compounds of the formula V can be made by methods well known in the art such as those described in PCT Patent Publication WO 98/58925 or reviewed in *The Organic Chemistry of Drug Synthesis*, D. Lednicer and L. A. Mitscher, Volume 1, pages 167 to 277 and references therein. Each of the above referenced publications and applications is hereby incorporated by reference in its entirety.

Compounds of the formula III are commercially available or can be made by methods well known to those skilled in the art.

The compounds of formula HX-Ar$^1$—Y—Z are commercially available or can be made by methods well known to those skilled in the art.

Scheme 2 refers to the preparation of compounds of the formula I in a three-step synthesis from compounds of the formula VI or VII. Referring to Scheme 2, a compound of the formula I is prepared from a compound of the formula IX by reaction with a suitable base and a suitable alkylating agent of the formula $R^1L^4$ in the presence of a solvent. Suitable bases include sodium hydride, potassium carbonate, sodium carbonate, triethylamine, pyridine or triethanolamine; most preferably sodium hydride. Suitable alkylating agents include those wherein $L^4$ is halo, p-tolylsulfonyloxy (OTs) or methylsulfonyloxy (OMs), preferably halo, most preferably chloro or bromo; or alkylating agents include such compounds as Eshenmoser's Salts; epoxides or suitably substituted electrophilic aziridines. Suitable solvents depend upon the base used but may be chosen from N,N-dimethylformamide, tetrahydrofuran, acetonitrile and water. The aforesaid reaction is conducted at a temperature of about 0° C. to about 30° C. preferably about 20° C. to about 25° C. for a time period between about 15 minutes to about 16 hours.

A compound of the formula IX may be prepared from a compound of the formula VII by reaction with a urea of the formula

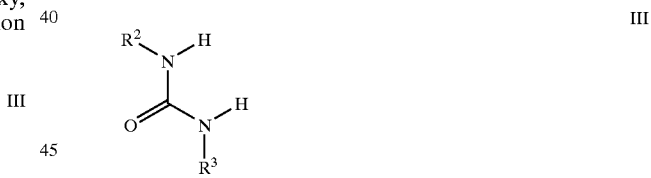   III in the presence of a strong base in a polar solvent. Suitable bases include sodium methoxide, sodium ethoxide and magnesium methoxide; preferably sodium ethoxide. Suitable solvents include alcohols (such as ethanol) or tetrahydrofuran, preferably absolute ethanol. The aforesaid reaction is conducted at a temperature of about 20° C. to about 90° C. preferably about 50° C. to about 65° C. for a time period between about 15 minutes to about 16 hours.

A compound of the formula VIII may be prepared from a compound of the formula VI, wherein $L^3$ is a leaving group such as halo, p-tolylsulfonyloxy (OTs) or methylsulfonyloxy (OMs), preferably halo, most preferably chloro, by reaction with a compound of the formula HX-Ar$^1$—Y—Z in the presence of a base in a polar solvent. Suitable bases include sodium methoxide, sodium ethoxide, potassium carbonate and sodium hydride; preferably sodium ethoxide. Suitable solvents include dimethylformamide (DMF), alcohols (such as ethanol) or tetrahydrofuran, preferably ethanol. The aforesaid reaction is conducted at a temperature of about 20° C. to about 90° C. preferably about 50° C. to about 70° C.

for a time period between about 15 minutes to about 16 hours, preferably about 3 hours. Reactions of this type are further illustrated by the method of J. B. Niederl and R. T. Roth, *J. Amer. Chem. Soc.*, 62,1154 (1940).

Alternatively, a compound of the formula VIII may also be prepared from a compound of the formula VII in the presence of a suitable catalyst, preferably rhodium(II)acetate according to the procedure described by M. Campbell et al., *Aust. J. Chem.*, 45, 2061 (1992).

Compounds of the formula VI and VII are commercially available or easily obtained from readily available starting materials according to methods well known to those skilled in the art. For example compounds of the Formula VII may be prepared according to the method of D. W. Peace et al, *Synthesis*, 658 (1971).

Compounds of the formula III are commercially available or can be prepared by methods well known to those skilled in the art.

Scheme 3 refers to the preparation of compounds of the formula I; in particular those wherein X is oxygen or —OCH$_2$—. Referring to Scheme 3, a compound of the formula I may be obtained by alkylation of a compound of the formula XI with a suitable phenol of the formula HOAr$^1$—Y—Z according to the method of O. Mitsonubu (*Synthesis*, 1 (1981)) or by alkylation with a suitable alkylating agent of the formula L$^3$CH$_2$Ar$^1$—Y—Z wherein L$^3$ is a leaving group such as halo, p-tolylsulfonyloxy (OTs) or methylsulfonyloxy (OMs), preferably halo, most preferably chloro or bromo in a suitable solvent such as N,N-dimethylformamide, tetrahydrofuran, acetonitrile in the presence of a suitable base such as sodium hydride, potassium carbonate, triethylamine, pyridine or triethanolamine. The aforesaid reaction is conducted at a temperature of about 0° C. to about 50° C. preferably about 20° C. for a time period between about 15 minutes to about 16 hours.

Compounds of the formula XI may be prepared from compounds of the formula X according to the method of J. A. Vida et al., *J. Med. Chem.*, 17, 732 (1974).

Compounds of the formula X may be prepared from a compound of the formula XII by reaction with a suitable base, in the presence of a suitable alkylating agent R$^1$L$^4$ and a solvent, such as described in Biehl et al., *J.Het.Chem.*, 23, 9 (1986). Suitable bases include sodium hydride, potassium carbonate, triethylamine, pyridine, triethanolamine; most preferably triethanolamine. Suitable alkylating agents include those wherein L$^4$ is halo, p-tolylsulfonyloxy (OTs) or methylsulfonyloxy (OMs), preferably halo, most preferably chloro or bromo; or alkylating agents such as Eshenmosers Salt; epoxides or suitably substituted electrophilic aziridines. Suitable solvents depend upon the base used but may be chosen from N,N-dimethylformamide, tetrahydrofuran, acetonitrile and water. The aforesaid reaction is conducted at a temperature of about 0° C. to about 30° C. preferably about 20° C. to about 25° C. for a time period between about 15 minutes to about 16 hours.

Compounds of the formula XII are commercially available or can be easily prepared by those skilled in the art according to the methods reviewed in *The Organic Chemistry of Drug Synthesis*, D. Lednicer and L. A. Mitscher, Volume 1, pages 167 to 277 and references cited therein.

Scheme 4 refers to the preparation of compounds of the formula I, wherein X is sulfur or —SCH$_2$—, or their oxidized derivatives >SO$_2$, >SO, —SO$_2$CH$_2$—, —SOCH$_2$—. Referring to Scheme 4, such a compound of the formula I may be obtained by alkylation of the pyrimidine-2,4,6-trione ring of a compound of the formula XIV (wherein R$^2$ and R$^3$ are hydrogen) with a suitable alkylating agent L$^3$R$^2$ or L$^3$R$^3$ wherein L$^3$ is a leaving group such as halo, p-tolylsulfonyloxy (OTs) or methylsulfonyloxy (OMs), preferably halo, most preferably chloro or bromo in a suitable solvent such as N,N-dimethylformamide, tetrahydrofuran, acetonitrile in the presence of a suitable base such as sodium hydride, potassium carbonate, triethylamine, pyridine or triethanolamine. The aforesaid reaction is conducted at a temperature of about 20° C. to about 70° C. preferably about 20° C. for a time period between about 15 minutes to about 16 hours.

Compounds of the formula XIV, may be prepared by alkylation of a compound of the formula X with a suitable disulfide of the formulae (SAr$^1$—Y—Z)$_2$ or (SCH$_2$Ar$^1$—Y—Z)$_2$ in a suitable solvent such as N,N-dimethylformamide, tetrahydrofuran, acetonitrile in the presence of a suitable base, such as sodium hydride, potassium carbonate, triethylamine, pyridine or triethanolamine. The aforesaid reaction is conducted at a temperature of about 20° C. to about 70° C. preferably about 20° C. for a time period between about 15 minutes to about 16 hours.

Disulfides (SAr$^1$—Y—Z)$_2$ or (SCH$_2$Ar$^1$—Y—Z)$_2$ may be prepared from the corresponding thiols HSAr$^1$—Y—Z or HSCH$_2$Ar$^1$—Y—Z by oxidative methods well known to those skilled the art.

Compounds of the formula X are commercially available or can be made by methods well known to those skilled in the art.

The compounds of the formula I, which are basic in nature, are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure.

Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

BIOLOGICAL ASSAYS

The ability of the compounds of formula I or their pharmaceutically acceptable salts (hereinafter also referred to as the compounds of the present invention) to inhibit metalloproteinases or mammalian reprolysin and, consequently, demonstrate their effectiveness for treating diseases characterized by metalloproteinase or the mammalian reprolysin activity (such as the production of tumor necrosis factor) is shown by the following in vitro assay tests.

MMP Assays

Collagenase-3 (matrix metalloproteinase-13) selective inhibitors as used herein refer to agents which exhibit at least a 100 fold selectivity for the inhibition of collagenase-3 enzyme activity over collagenase-1 enzyme activity and a potency of less than 100 nM as defined by the $IC_{50}$ results from the MMP-13/MMP-1 fluorescence assays described below. Collagenase-3 selective inhibitors can be identified by screening the inhibitors of the present invention through the MMP-13/MMP-1 fluorescence assays described below and selecting those agents with MMP-13/MMP-1 inhibition $IC_{50}$ ratios of 100 or greater and potency of less than 100 nM.

Non-selective collagenase inhibitors as used herein refer to agents which exhibit less than a 100 fold selectivity for the inhibition of collagenase-3 enzyme activity over collagenase-1 enzyme activity or a potency of more than 100 nM as defined by the $IC_{50}$ results from the MMP-13/MMP-1 fluorescence assays described below.

The ability of collagenase inhibitors to inhibit collagenase activity is well known in the art. The following assays may be used to identify matrix metalloproteinase inhibitors.

Inhibition of Human Collagenase (MMP-1)

Human recombinant collagenase is activated with trypsin. The amount of trypsin is optimized for each lot of collagenase-1 but a typical reaction uses the following ratio: 5 μg trypsin per 100 μg of collagenase. The trypsin and collagenase are incubated at room temperature for 10 minutes then a five fold excess (50 mg/10 mg trypsin) of soybean trypsin inhibitor is added.

Stock solutions (10 mM) of inhibitors are made up in dimethylsulfoxide and then diluted using the following scheme:

10 mM→120 μM→12 μM→1.2 μM→0.12 μM

Twenty-five microliters of each concentration is then added in triplicate to appropriate wells of a 96 well microfluor plate. The final concentration of inhibitor will be a 1:4 dilution after addition of enzyme and substrate. Positive controls (enzyme, no inhibitor) are set up in wells D7–D12 and negative controls (no enzyme, no inhibitors) are set in wells D1-D6.

Collagenase-1 is diluted to 240 ng/ml and 25 μl is then added to appropriate wells of the microfluor plate. Final concentration of collagenase in the assay is 60 ng/ml.

Substrate (DNP-Pro-Cha-Gly-Cys(Me)-His-Ala-Lys (NMA)-NH$_2$) is made as a 5 mM stock in dimethylsulfoxide and then diluted to 20 μM in assay buffer. The assay is initiated by the addition of 50 μl substrate per well of the microfluor plate to give a final concentration of 10 μM.

Fluorescence readings (360 nM excitation, 460 nm emission) are taken at time 0 and then at 20 minute intervals. The assay is conducted at room temperature with a typical assay time of 3 hours Fluorescence versus time is then plotted for both the blank and collagenase containing samples (data from triplicate determinations is averaged). A time point that provides a good signal (at least five fold over the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration versus % control (inhibitor fluorescence divided by fluorescence of collagenase alone× 100). $IC_{50}$'s are determined from the concentration of inhibitor that gives a signal that is 50% of the control.

If $IC_{50}$'s are reported to be less than 0.03 μM then the inhibitors are assayed at concentrations of 0.3 μM, 0.03 μM, and 0.003 μM.

Inhibition of Gelatinase (MMP-2)

Human recombinant 72 kD gelatinase (MMP-2, gelatinase A) is activated for 16–18 hours with 1 mM p-aminophenyl-mercuric acetate (from a freshly prepared 100 mM stock in 0.2 N NaOH) at 4° C., rocking gently.

10 mM dimethylsulfoxide stock solutions of inhibitors are diluted serially in assay buffer (50 mM TRIS, pH 7.5, 200 mM NaCl, 5 mM CaCl$_2$, 20 μM ZnCl$_2$ and 0.02% BRIJ-35 (vol./vol.)) using the following scheme:

10 mM→120 μM→12 μM→1.2 μM→0.12 μM

Further dilutions are made as necessary following this same scheme. A minimum of four inhibitor concentrations for each compound are performed in each assay. 25 μL of each concentration is then added to triplicate wells of a black 96 well U-bottomed microfluor plate. As the final assay volume is 100 μL, final concentrations of inhibitor are the result of a further 1:4 dilution (i.e. 30 μM→3 μM→0.3 μM→0.03 μM, etc.). A blank (no enzyme, no inhibitor) and a positive enzyme control (with enzyme, no inhibitor) are also prepared in triplicate.

Activated enzyme is diluted to 100 ng/mL in assay buffer, 25 μL per well is added to appropriate wells of the microplate. Final enzyme concentration in the assay is 25 ng/mL (0.34 nM).

A five mM dimethylsulfoxide stock solution of substrate (Mca-Pro-Leu-Gly-Leu-Dpa-Ala-Arg-NH$_2$) is diluted in assay buffer to 20 μM. The assay is initiated by addition of 50 μL of diluted substrate yielding a final assay concentration of 10 μM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Stromelysin Activity (MMP-3)

Human recombinant stromelysin (MMP-3, stromelysin-1) is activated for 20–22 hours with 2 mM p-aminophenyl-mercuric acetate (from a freshly prepared 100 mM stock in 0.2 N NaOH) at 37° C.

10 mM dimethylsulfoxide stock solutions of inhibitors are diluted serially in assay buffer (50 mM TRIS, pH 7.5,150 mM NaCl, 10 mM $CaCl_2$ and 0.05% BRIJ-35 (vol./vol.)) using the following scheme:

10 mM→120 µM→12 µM→1.2 µM→0.12 µM

Further dilutions are made as necessary following this same scheme. A minimum of four inhibitor concentrations for each compound are performed in each assay. 25 µL of each concentration is then added to triplicate wells of a black 96 well U-bottomed microfluor plate. As the final assay volume is 100 µL, final concentrations of inhibitor are the result of a further 1:4 dilution (i.e. 30 µM→3 µM→0.3 µM→0.03 µM, etc.). A blank (no enzyme, no inhibitor) and a positive enzyme control (with enzyme, no inhibitor) are also prepared in triplicate.

Activated enzyme is diluted to 200 ng/mL in assay buffer, 25 µL per well is added to appropriate wells of the microplate. Final enzyme concentration in the assay is 50 ng/mL (0.875 nM).

A ten mM dimethylsulfoxide stock solution of substrate (Mca-Arg-Pro-Lys-Pro-Val-Glu-Nva-Trp-Arg-Lys(Dnp)-$NH_2$) is diluted in assay buffer to 6 µM. The assay is initiated by addition of 50 µL of diluted substrate yielding a final assay concentration of 3 µM substrate. At time zero, fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The zero time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of Human 92 kD Gelatinase (MMP-9)

Inhibition of 92 kD gelatinase (MMP-9) activity is assayed using the Mca-Pro-Leu-Gly-Leu-Dpa-Ala-Arg-$NH_2$ substrate (10 µM) under similar conditions as described above for the inhibition of human collagenase (MMP-1).

Human recombinant 92 kD gelatinase (MMP-9, gelatinase B) is activated for 2 hours with 1 mM p-aminophenyl-mercuric acetate (from a freshly prepared 100 mM stock in 0.2 N NaOH) at 37 C.

10 mM dimethylsulfoxide stock solutions of inhibitors are diluted serially in assay buffer (50 mM TRIS, pH 7.5, 200 mM NaCl, 5 mM $CaCl_2$, 20 µM $ZnCl_2$, 0.02% BRIJ-35 (vol./vol.)) using the following scheme:

10 mM→120 µM→12 µM→1.2 µM→0.12 µM

Further dilutions are made as necessary following this same scheme. A minimum of four inhibitor concentrations for each compound are performed in each assay. 25 µL of each concentration is then added to triplicate wells of a black 96 well U-bottomed microfluor plate. As the final assay volume is 100 µL, final concentrations of inhibitor are the result of a further 1:4 dilution (i.e. 30 µM→3 µM→0.3 µM→0.03 µM, etc.). A blank (no enzyme, no inhibitor) and a positive enzyme control (with enzyme, no inhibitor) are also prepared in triplicate.

Activated enzyme is diluted to 100 ng/mL in assay buffer, 25 µL per well is added to appropriate wells of the microplate. Final enzyme concentration in the assay is 25 ng/mL (0.27 nM).

A five mM dimethylsulfoxide stock solution of substrate (Mca-Pro-Leu-Gly-Leu-Dpa-Ala-Arg-$NH_2$) is diluted in assay buffer to 20 µM. The assay is initiated by addition of 50 µL of diluted substrate yielding a final assay concentration of 10 µM substrate. A 0 time fluorescence reading (320 excitation; 390 emission) is immediately taken and subsequent readings are taken every fifteen minutes at room temperature with a PerSeptive Biosystems CytoFluor Multi-Well Plate Reader with the gain at 90 units.

The average value of fluorescence of the enzyme and blank are plotted versus time. An early time point on the linear part of this curve is chosen for $IC_{50}$ determinations. The 0 time point for each compound at each dilution is subtracted from the latter time point and the data then expressed as percent of enzyme control (inhibitor fluorescence divided by fluorescence of positive enzyme control× 100). Data is plotted as inhibitor concentration versus percent of enzyme control. $IC_{50}$'s are defined as the concentration of inhibitor that gives a signal that is 50% of the positive enzyme control.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 µM zinc chloride, 0.02% brij). Twenty-five microliters of diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solutions of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 µM, 3 µM, 0.3 µM, and 0.03 µM.

Substrate (Dnp-Pro-Cha-Gly-Cys(Me)-His-Ala-Lys (NMA)-$NH_2$) is prepared as for inhibition of human collagenase (MMP-1) and 50 µis added to each well to give a final assay concentration of 10 µM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03

μM, inhibitors are then assayed at final concentrations of 0.3 μM, 0.03 μM, 0.003 μM and 0.0003 μM.

Collagen Film MMP-13 Assay

Rat type I collagen is radiolabeled with $^{14}$C acetic anhydride (T. E. Cawston and A. J. Barrett, *Anal. Biochem.*, 99, 340–345 (1979)) and used to prepare 96 well plates containing radiolabeled collagen films (Barbara Johnson-Wint, *Anal. Biochem.*, 104, 175–181 (1980)). When a solution containing collagenase is added to the well, the enzyme cleaves the insoluble collagen which unwinds and is thus solubilized. Collagenase activity is directly proportional to the amount of collagen solubilized, determined by the proportion of radioactivity released into the supernatant as measured in a standard scintillation counter. Collagenase inhibitors are, therefore, compounds which reduce the radioactive counts released with respect to the controls with no inhibitor present. One specific embodiment of this assay is described in detail below.

For determining the selectivity of compounds for MMP-13 versus MMP-1 using collagen as a substrate, the following procedure is used. Recombinant human proMMP-13 or proMMP-1 is activated according to the procedures outlined above. The activated MMP-13 or MMP-1 is diluted to 0.6 ug/ml with buffer (50 mM Tris pH 7.5, 150 mM NaCl, 10 mM $CaCl_2$, 1 uM $ZnCl_2$, 0.05% Brij-35, 0.02% sodium azide).

Stock solutions of test compound (10 mM) in dimethylsulfoxide are prepared. Dilutions of the test compounds in the Tris buffer, above, are made to 0.2, 2.0, 20, 200, 2000 and 20000 nM.

100 μl of appropriate drug dilution and 100 μl of diluted enzyme are pipetted into wells of a 96 well plate containing collagen films labeled with $^{14}$C-collagen. The final enzyme concentration is 0.3 μg/ml while the final drug concentration is 0.1, 1.0, 10, 100, 1000 nM. Each drug concentration and control is analyzed in triplicate. Triplicate controls are also run for the conditions in which no enzyme is present and for enzyme in the absence of any compound.

The plates are incubated at 37° C. for a time period such that around 30–50% of the available collagen is solubilized—determined by counting additional control wells at various time points. In most cases around 9 hours of incubation are required. When the assay has progressed sufficiently, the supernatant from each well is removed and counted in a scintillation counter. The background counts (determined by the counts in the wells with no enzyme) are subtracted from each sample and the % release calculated in relation to the wells with enzyme only and no inhibitor. The triplicate values for each point are averaged and the data graphed as percent release versus drug concentration. $IC_{50}$'s are determined from the point at which 50% inhibition of release of radiolabeled collagen is obtained.

To determine the identity of the active collagenases in cartilage conditioned medium, assays were carried out using collagen as a substrate, cartilage conditioned medium containing collagenase activity and inhibitors of varying selectivity. The cartilage conditioned medium was collected during the time at which collagen degradation was occurring and thus is representative of the collagenases responsible for the collagen breakdown. Assays were carried out as outlined above except that instead of using recombinant MMP-13 or recombinant MMP-1, cartilage conditioned medium was the enzyme source.

IL-1 Induced Cartilage Collagen Degradation From Bovine Nasal Cartilage

This assay uses bovine nasal cartilage explants which are commonly used to test the efficacy of various compounds to inhibit either IL-1 induced proteoglycan degradation or IL-1 induced collagen degradation. Bovine nasal cartilage is a tissue that is very similar to articular cartilage, i.e. chondrocytes surrounded by a matrix that is primarily type II collagen and aggrecan. The tissue is used because it: (1) is very similar to articular cartilage, (2) is readily available, (3) is relatively homogeneous, and (4) degrades with predictable kinetics after IL-1 stimulation.

Two variations of this assay have been used to assay compounds. Both variations give similar data. The two variations are described below:

Variation 1

Three plugs of bovine nasal cartilage (approximately 2 mm diameter×1.5 mm long) are placed into each well of a 24 well tissue culture plate. One ml of serumless medium is then added to each well. Compounds are prepared as 10 mM stock solutions in DMSO and then diluted appropriately in serumless medium to final concentrations, e.g., 50, 500 and 5000 nM. Each concentration is assayed in triplicate.

Human recombinant IL-1α (5ng/mL) (IL-1) is added to triplicate control wells and to each well containing drug. Triplicate control wells are also set up in which neither drug nor IL-1 are added. The medium is removed and fresh medium containing IL-1 and the appropriate drug concentrations is added on days 6, 12, 18 and 24 or every 3–4 days if necessary. The media removed at each time point is stored at −20° C. for later analysis. When the cartilage in the IL-1 alone wells has almost completely resorbed (about day 21), the experiment is terminated. The medium, is removed and stored. Aliquots (100 ul) from each well at each time point are pooled, digested with papain and then analyzed for hydroxyproline content. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot.

Variation 2

The experimental set-up is the same as outlined above in Variation 1, until day 12. On day 12, the conditioned medium from each well is removed and frozen. Then one ml of phosphate buffered saline (PBS) containing 0.5 μg/ml trypsin is added to each well and incubation continued for a further 48 hours at 37° C. After 48 hours incubation in trypsin, the PBS solution is removed. Aliquots (50 μl) of the PBS/trypsin solution and the previous two time points (days 6 and 12) are pooled, hydrolyzed and hydroxyproline content determined. Background hydroxyproline (average of wells with no IL-1 and no drug) is subtracted from each data point and the average calculated for each triplicate. The data is then expressed as a percent of the IL-1 alone average value and plotted. The $IC_{50}$ is determined from this plot. In this variation, the time course of the experiment is shortened considerably. The addition of trypsin for 48 hours after 12 days of IL-1 stimulation likely releases any type II collagen that has been damaged by collagenase activity but not yet released from the cartilage matrix. In the absence of IL-1 stimulation, trypsin treatment produces only low background levels of collagen degradation in the cartilage explants.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human Monocyte Assay

Human mononuclear cells were isolated from anti-coagulated human blood using a one-step Ficoll-hypaque separation technique. (2) The mononuclear cells were washed three times in Hanks balanced salt solution (HBSS) with divalent cations and resuspended to a density of $2\times10^6$/ml in HBSS containing 1% BSA. Differential counts determined using the Abbott Cell Dyn 3500 analyzer indicated that monocytes ranged from 17 to 24% of the total cells in these preparations.

180 μl of the cell suspension was aliquoted into flat bottom 96 well plates (Costar). Additions of compounds and LPS (100 ng/ml final concentration) gave a final volume of 200 μl. All conditions were performed in triplicate. After a four hour incubation at 37° C. in an humidified $CO_2$ incubator, plates were removed and centrifuged (10 minutes at approximately 250×g) and the supernatants removed and assayed for TNFa using the R&D ELISA Kit.

Aggrecanase Assay

Primary porcine chondrocytes from articular joint cartilage are isolated by sequential trypsin and collagenase digestion followed by collagenase digestion overnight and are plated at $2\times10^5$ cells per well into 48 well plates with 5 μCi/ml $^{35}$S (1000 Ci/mmol) sulphur in type I collagen coated plates. Cells are allowed to incorporate label into their proteoglycan matrix (approximately 1 week) at 37° C., under an atmosphere of 5% $CO_2$.

The night before initiating the assay, chondrocyte monolayers are washed two times in DMEM/1% PSF/G and then allowed to incubate in fresh DMEM/1% FBS overnight.

The following morning chondrocytes are washed once in DMEM/1% PSF/G. The final wash is allowed to sit on the plates in the incubator while making dilutions.

| | |
|---|---|
| Control Media | DMEM alone (control media) |
| IL-1 Media | DMEM + IL-1 (5 ng/ml) |
| Drug Dilutions | Make all compounds stocks at 10 mM in DMSO. Make a 100 uM stock of each compound in DMEM in 96 well plate. Store in freezer overnight. The next day perform serial dilutions in DMEM with IL-1 to 5 uM, 500 nM, and 50 nM. Aspirate final wash from wells and add 50 ul of compound from above dilutions to 450 ul of IL-1 media in appropriate wells of the 48 well plates. Final compound concentrations equal 500 nM, 50 nM, and 5 nM. All samples completed in triplicate with Control and IL-1 alone samples on each plate. |

Plates are labeled and only the interior 24 wells of the plate are used. On one of the plates, several columns are designated as IL-1 (no drug) and Control (no IL-1, no drug). These control columns are periodically counted to monitor 35S-proteoglycan release. Control and IL-1 media are added to wells (450 ul) followed by compound (50 ul) so as to initiate the assay. Plates are incubated at 37° C., with a 5% $CO_2$ atmosphere.

At 40–50% release (when CPM from IL-1 media is 4–5 times control media) as assessed by liquid scintillation counting (LSC) of media samples, the assay is terminated (9–12 hours). Media is removed from all wells and placed in scintillation tubes. Scintillate is added and radioactive counts are acquired (LSC). To solubilize cell layers, 500 ul of papain digestion buffer (0.2 M Tris, pH 7.0, 5 mM EDTA, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC).

The percent of released counts from the total present in each well is determined. Averages of the triplicates are made with control background subtracted from each well. The percent of compound inhibition is based on IL-1 samples as 0% inhibition (100% of total counts).

The compounds of the present invention that were tested all have $IC_{50}$'s in at least one of the above assays of less than 100 μm preferably less than 100 nM. Certain preferred groups of compounds possess differential selectivity toward the various MMP's or ADAMs. One group of preferred compounds possess selective activity towards MMP-13 over MMP-1. Another preferred group of compounds possess aggrecanase activity more preferably in addition to selectivity for MMP-13 over MMP-1.

For administration to mammals, including humans, for the inhibition of matrix metalloproteinases or mammalian reprolysin, a variety of conventional routes may be used including oral, parenteral (e.g., intravenous, intramuscular or subcutaneous), buccal, anal and topical. In general, the compounds of the invention (hereinafter also known as the active compounds) will be administered at dosages between about 0.1 and 25 mg/kg body weight of the subject to be treated per day, preferably from about 0.3 to 5 mg/kg. Preferably the active compound will be administered orally or parenterally. However, some variation in dosage will necessarily occur depending on the condition of the subject being treated. The person responsible for administration will, in any event, determine the appropriate dose for the individual subject.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure or in vacuo means that a rotary evaporator was used.

EXAMPLE 1

5-Methyl, 5-(4'-Phenoxy-phenoxy)-pyrimidine-2,4,6-trione

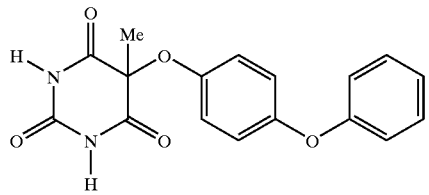

Sodium (190 mg, 8.26 mM) was slowly and carefully added to absolute ethanol (25 ml) and stirred until the solution was homogeneous. Urea (620 mg, 10.32 mM) was added and the mixture stirred for 30 minutes. A solution of diethyl-2-methyl-2-(4'-phenoxy-phenoxy)malonate (1.48 gm, 4.13 mM) in absolute ethanol (25 ml) was added dropwise and the resultant mixture heated under reflux (6 hours). The reaction was allowed to cool to room temperature, evaporated to dryness and partitioned between ethylacetate (100 ml) and water (100 ml). The aqueous layer was separated, acidified to $pH_1$ with aqueous 1N HCl and extracted with ethyl acetate (3×100 ml). The combined organic extracts were dried over magnesium sulfate ($MgSO_4$), filtered and evaporated to dryness. The resultant white powder was crystallized from hot methylene chloride to give the target compound as a white crystalline material (310 mg; see Table 1 for analytical data).

EXAMPLES 2 TO 9

Examples 2–9 were prepared by a similar procedure to that described above except that diethyl-2-methyl-2-(4'-phenoxy-phenoxy)malonate was replaced with the appropriately substituted malonate. In the table that follows, Me is methyl, Bu in n-butyl, Ex. No. is Example Number, and m/z is a low resolution molecular ion weight.

TABLE 1

| Ex. No. | Structure | m/z | NMR data (400 MHz) | Melting Point ° C. |
|---|---|---|---|---|
| 1 | 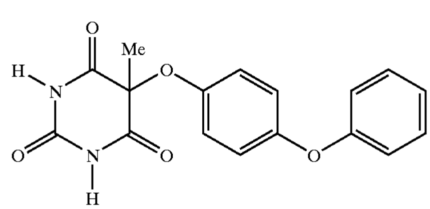 | 325.2 | δ($d^6$-acetone); 1.95(s,3H); 2.85(s, br, 2H); 6.85–7.00(m, 6H); 7.05(m, 1H); 7.30–7.35(m, 2H). | 182 |

TABLE 1-continued

| Ex. No. | Structure | m/z | NMR data (400 MHz) | Melting Point ° C. |
|---|---|---|---|---|
| 2 | 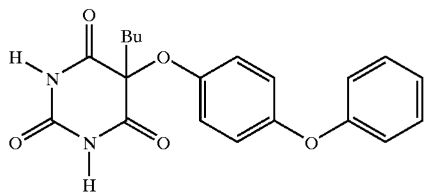 | 367.3 | δ(d⁶-acetone); 0.95(t, 3H); 1.40(m, 2H); 1.55(m, 2H); 2.25(m, 2H); 2.85(s, br, 2H); 6.82–7.00(m, 6H); 7.05(m, 1H); 7.10–7.15(m, 2H). | 59–60 |
| 3 | 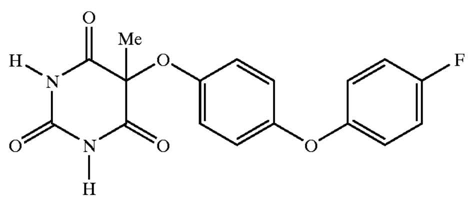 | 343.2 | δ(d⁶-acetone); 1.95(s, 3H); 2.85(s, br, 2H); 6.85–7.00(m, 6H), 7.10–7.15 9m, 2H). | 187–9 |
| 4 | 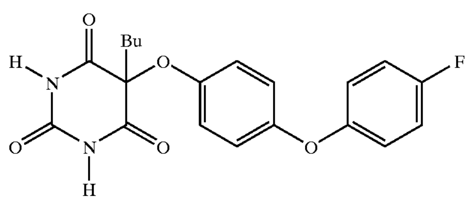 | 385.2 | δ(d⁶-acetone); 0.95(t, 3H); 1.40(m, 2H); 1.55(m, 2H); 2.25(m, 2H); 2.85(s, br, 2H); 6.82–7.00(m, 6H), 7.10–7.15(m, 2H). | 183 |
| 5 | 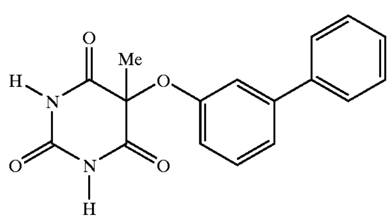 | 309.3 | δ(d⁶-acetone); 1.97(s, 3H); 2.90(s, br, 2H); 6.75–6.78(dd, 1H); 7.061–7.067(m, 1H); 7.27–7.46(m, 5H); 7.57–7.59(d, 2H). | 175 |
| 6 | 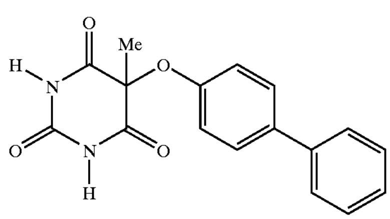 | 309.3 | δ(d⁶-acetone); 1.95(s, 3H); 6.86–6.89(dd, 1H); 7.27–7.62(m, 8H). | 200–202 |
| 7 | 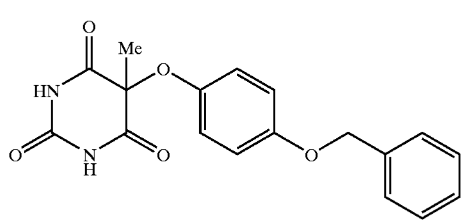 | 339.1 | δ(d⁶-acetone); 1.88(s, 3H); 5.03(s, 2H), 6.77–6.91(m, 4H); 7.30–7.45(m, 5H). | — |

PREPARATION 1

Diethyl-2-n-butyl, 2-(4'-Phenoxy-phenoxy)malonate

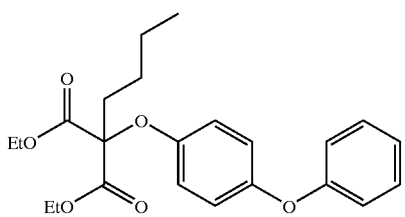

Sodium (112 mg) was added slowly and carefully to absolute ethanol (25 ml) and stirred until a homogeneous solution was observed. 4-phenoxyphenol (910 mg) (Aldrich Chemical Company) was added slowly and the resultant mixture stirred (30 min, room temperature); diethyl-α-bromo-α-n-butyl-malonate (1.44 gm) (See Preparation 3) in absolute ethanol (25 ml) was added dropwise and the resultant mixture heated to reflux (1 hour). The reaction mixture was cooled to room temperature, evaporated to dryness and partitioned between ethyl acetate (100 ml) and water (100 ml). The organic layer was separated, washed with water (3×100 ml), dried (magnesium sulfate), filtered and evaporated to give the desired compound as a clear oil (1.82 gm). $^1$H NMR (CDCl$_3$): δ=0.85–0.88 (t, 3H); 1.21–1.25 (t, 6H); 1.31–1.39 (m, 4H); 2.2–2.27 (m, 2H); 4.23–4.28 (q, 4H); 6.80–6.95 (m, 6H); 7.03–7.08 (t, 1H); 7.25–7.31 (q, 2H); m/z=401 (M$^+$).

PREPARATION 2

Diethyl-2-methyl, 2-(4'-phenoxy-phenoxy)malonate

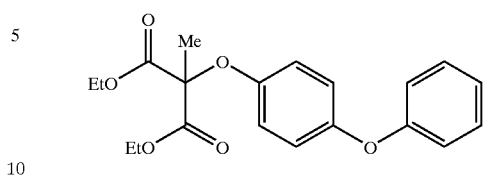

Sodium (112 mg) was added slowly and carefully to absolute ethanol (25 ml) and stirred until a homogeneous solution was observed. 4-Phenoxyphenol (910 mg) (Aldrich Chemical Company) was added slowly and the resultant mixture stirred (30 minutes, room temperature); diethyl-α-bromo-α-methyl malonate (1.23 gm) (Aldrich Chemical Company) in absolute ethanol (25 ml) was added dropwise and the resultant mixture heated to reflux (1 hour). The reaction mixture was cooled to room temperature, evaporated to dryness and partitioned between ethyl acetate (100 ml) and water (100 ml). The organic layer was separated, washed with water (3×100 ml), dried (magnesium sulfate), filtered and evaporated to give the desired compound as a clear oil (1.48 gm). $^1$H nmr (CDCl$_3$): δ=1.25–1.28 (t, 6H); 1.71 (s, 3H); 4.24–4.30 (q, 4H); 6.88–6.97 (m, 6H); 7.04–7.08 (t, 1H); 7.25–7.32 (q, 2H); m/z=359 (M$^+$).

Malonates including those contained in Table 2 were prepared using analogous procedures to those described above (preparations 1 and 2) starting from the appropriate α-bromo, α-alkyl malonate and the appropriate phenol. In the table that follows, Me is methyl and Et is ethyl.

TABLE 2

| Structure | $^1$H NMR | m/z |
|---|---|---|
| ![structure] | δ(d$^6$-acetone); 1.19–1.23(t, 6H); 1.64(s, 3H); 4.19–4.24(q, 4H); 6.90–7.14(m, 9H). | 377.2 |
| ![structure] | δ(d$^3$-chloroform); 0.86–0.88(t, 3H); 1.21–1.23(t, 6H); 1.25–1.38(m, 4H); 2.18–2.22(m, 2H); 4.20–4.25(q, 4H); 6.80–7.00(m, 8H). | 419.3 |
| ![structure] | δ(d$^6$-acetone); 1.19–1.23(t, 6H); 1.75(s, 3H); 4.24–4.29(q, 4H); 6.95–7.63(m, 9H). | 343.3 |

TABLE 2-continued

| Structure | ¹H NMR | m/z |
|---|---|---|
| 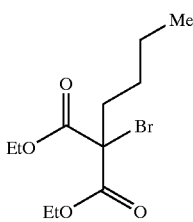 | δ(d⁶-acetone); 1.19–1.22(t, 6H); 1.72(s, 3H); 4.23–4.26(q, 4H); 6.89–7.60(m, 9H). | 343.3 |

PREPARATION 3

Diethyl-α-bromo-α-n-butylmalonate

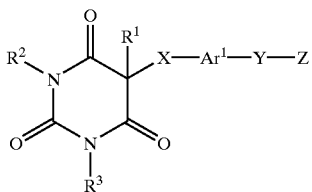

Diethyl-n-butylmalonate (32.2 gm) was dissolved in methylene chloride (200 ml) and treated, dropwise, with a solution of bromine (24.0 gm) dissolved in methylene chloride (25 ml). The resultant mixture was stirred (1 hour, room temperature) whereupon an orange coloration persisted. The solvent was removed under vacuum, and the residue distilled under high vacuum to give the desired product as a clear oil (boiling point temperature 105° C. to 110° C.; 36.0 gm). ¹H NMR (CDCl₃): δ=0.89–0.92 (t, 3H); 1.25–1.29 (t, 6H); 1.35–1.37 (m, 4H); 2.2–2.26 (m, 2H); 4.23–4.29 (q, 4H); m/z=295 and 297 (M⁺).

What is claimed is:

1. A compound of the formula $$R^2\text{-N}\cdots\text{N-R}^3 \text{ with } R^1, X\text{—}Ar^1\text{—}Y\text{—}Z$$

wherein $R^1$ is hydrogen, $(C_1-C_4)$perfluoroalkyl, $(C_1-C_8)$ alkyl, $(C_3-C_8)$cycloalkyl, tetrahydrofuranyl, tetrahydropyranyl, N-methyl-3-azetidinyl, piperazinyl, piperidinyl, 1,3-oxazolidin-4-on-5-yl, 1,3-oxazolidin-2,4-dion-5-yl, 4,5-dihydro-1,2-oxazolidin-3-on-4-yl, 1,3-thiazolidin-4-on-5-yl, 1,3-thiazolidin-2,4-dion-5-yl, 1,3-imidazolidin-4-on-5-yl, 1,3-imidazolidin-2,4-dion-5-yl, 1,2-pyrazolidin-3-on-4-yl, tetrahydro-1,3-oxazin-4-on-5-yl, tetrahydro-1,3-oxazin-2,4-dion-5-yl, morpholinyl, morpholin-3-on-2-yl, morpholin-3,5-dion-2-yl, 2,3-dihydro-1,4-oxazin-3-on-2-yl, tetrahydro-1,3-thiazin-4-on-5-yl, tetrahydro-1,3-thiazin-2,4-dion-5-yl, thiomorpholinyl, thiomorpholin-3-on-2-yl, thiomorpholin-3,5-dion-2-yl, 2,3-dihydro-1,4-thiazin-3-on-2-yl, hexahydro-1,2-diazin-3-on-4-yl, 4,5-dihydro-2H-pyridazin-3-on-4-yl, hexahydro-1,3-diazin-2,4-dion-5-yl, piperazin-2-on-3-yl, piperazin-2,6-dion-3-yl, tetrahydro-1,3,4-thiadiazin-5-on-6-yl, 5,6-dihydro-1,3,4-thiadiazin-5-on-6-yl, 1,3,4-oxadiazin-5-on-6-yl, 5,6-dihydro-1,2,4-oxadiazin-5-on-6-yl, tetrahydro-1,2,4-oxadiazin-5-on-6-yl, 1,2,4-triazin-5-on-6-yl, tetrahydro-1,2,4-oxadiazin-5-on-6-yl, 5,6-dihydro-1-2,4-oxadiazin-5-on-6-yl, 1,2,4-oxadiazin-3,5-dion-6-yl, or 1,2,4-triazin-6-on-5-yl; wherein said $(C_1-C_8)$alkyl may optionally contain one to three heteroatoms independently selected from oxygen, $>NR^5$ and sulfur; wherein said $(C_1-C_8)$alkyl or $(C_3-C_8)$ cycloalkyl may also optionally be substituted by one to two substituents independently selected from $(C_1-C_4)$ alkyl, $(C_6-C_{10})$aryl, pyridyl, furyl, pyrroyl, thienyl, isothiazolyl, imidazoly, benzimidazolyl, tetrazolyl, pyrazinyl, pyrimidyl, quinolyl, isoquinolyl, benzofuryl, isobenzofuryl, benzothienyl, pyrazoly, indolyl, isoindolyl, purinyl, carbazolyl, isoxazolyl, thiazolyl, oxazolyl, benzthiazoly, benzoxazolyl, OH, $NH_2$, $(C_1-C_4)$alkylamino, di[$(C_1-C_4)$alkyl]amino, $(C_3-C_8)$ cycloalkylamino, $(C_3-C_8)$cycloalkyl$(C_1-C_4)$ alkylamino, $(C_1-C_4)$alkoxy, —$CONH_2$, —$CONHR^4$, —$CON(R^4)_2$, $(C_3-C_8)$cycloakyl, tetrahydrofuranyl, tetrahydropyrany, N-methyl-3-azetidinyl, piperazinyl, piperidinyl, 1,3-oxazolidin-4-on-5-yl, 1,3-oxazolidin-2,4-dion-5-yl, 4,5-dihydro-1,2-oxazolidin-3-on-4-yl, 1,3-thiazolidin-4-on-5-yl, 1,3-thiazolidin-2,4-dion-5-yl, 1,3-imidazolidin-4-on-5-yl, 1,3-imidazolidin-2,4-dion-5-yl, 1,2-pyrazolidin-3-on-4-yl, tetrahydro-1,3-oxazin-4-on-5-yl, tetrahydro-1,3-oxazin-2,4-dion-5-yl, morpholinyl, morpholin-3-on-2-yl, morpholin-3,5-dion-2-yl, 2,3-dihydro-1,4-oxazin-3-on-2-yl, tetrahydro-1,3-thiazin-4-on-5-yl, tetrahydro-1,3-thiazin-2,4-dion-5-yl, thiomorpholinyl, thiomorpholin-3-on-2-yl, thiomorpholin-3,5-dion-2-yl, 2,3-dihydro-1,4-thiazin-3-on-2-yl, hexahydro-1,2-diazin-3-on-4-yl, 4,5-dihydro-2H-pyridazin-3-on-4-yl, hexahydro-1,3-diazin-2,4-dion-5-yl, piperazin-2-on-3-yl, or piperazin-2,6-dion-3-yl;

$R^2$ and $R^3$ are hydrogen;

X is selected from the group consisting of oxygen, sulfur, $>SO_2$, $>S=O$, $>NR^4$, —$CH_2O$—, —$OCH_2$—, —$CH_2S$—, —$CH_2(S=O)$—, —$CH_2SO_2$—, —$SCH_2$—, —$SOCH_2$—, —$SO_2CH_2$—, —$(R^4)CH_2$—, —$CH_2N(R^4)$—, —$(R^4)SO_2$— and —$SO_2N(R^4)$—;

$R^4$ wherever it occurs is independently selected from hydrogen and $(C_1-C_4)$alkyl;

$R^5$ wherever it occurs is independently selected from hydrogen, $(C_1-C_4)$alkyl, $(C_6-C_{10})$aryl, pyridyl, furyl, pyrroyl, thienyl, isothiazolyl, imidazolyl, benzimidazolyl, tetrazolyl, pyrazinyl, pyrimidy, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl, benzoxazolyl, OH, —CONH$_2$, —CONHR$^4$, —CON(R$^4$)$_2$ and (C$_3$–C$_8$)cycloalkyl;

Y is selected from the group consisting of a bond, oxygen, sulfur, >SO$_2$, >S=O, >NH, —CH$_2$—, —CH$_2$O—, —OCH$_2$—, —CH$_2$S—, —CH$_2$(S=O)—, —CH$_2$SO$_2$—, —SCH$_2$—, —SOCH$_2$—, —SO$_2$CH$_2$—, —NHCH$_2$—, —CH$_2$NH—, —$_2$CH$_2$—, —CH=CH—, —NHSO$_2$— —SO$_2$NH—;

Ar$^1$ is (C$_6$–C$_{10}$)aryl, pyridyl, furyl, pyrroyl, thienyl, isothiazolyl, imidazolyl, benzimidazolyl, tetrazolyl, pyrazinyl, pyrimidyl, quinoly, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl; and Z is (C$_6$–C$_{10}$)aryl, (C$_3$–C$_8$)cycloalkyl, (C$_3$–C$_8$)cycloalky (C$_1$–C$_4$)alkyl, pyridyl, furyl, pyrroyl, isothiazolyl, imidazolyl, benzimidazolyl, tetrazolyl, pyrazinyl, pyrimidyl, quinolyl, isoquinolyt, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl; wherein said (C$_3$–C$_8$)cycloalkyl moiety of said (C$_3$–C$_8$)cycloalkyl or (C$_3$–C$_8$)cycloalkyl(C$_1$–C$_4$)alkyl may optionally be replaced by tetrahydrofuranyl, tetrahydropyranyl, N-methyl-3-azetidinyl, piperazinyl, piperidinyl, 1,3-oxazolidin-4-on-5-yl, 1,3-oxazolidin-2,4-dion-5-yl, 4,5-dihydro-1,2-oxazolidin-3-on-4-yl, 1,3-thiazolidin-4-on-5-yl, 1,3-thiazolidin-2,4-dion-5-yl, 1,3-imidazolidin-4-on-5-yl, 1,3-imidazolidin-2,4-dion-5-yl, 1,2-pyrazolidin-3-on-4-yl, tetrahydro-1,3-oxazin-4-on-5-yl, tetrahydro-1,3-oxazin-2,4-dion-5-yl, morpholinyl, morpholin-3-on-2-yl, morpholin-3,5-dion-2-yl, 2,3-dihydro-1,4-oxazin-3-on-2-yl, tetrahydro-1,3-thiazin-4-on-5-yl, tetrahydro-1,3-thiazin-2,4-dion-5-yl, thiomorpholinyl, thiomorpholin-3-on-2-yl, thiomorpholin-3,5-dion-2-yl, 2,3-dihydro-1,4-thiazin-3-on-2-yl, hexahydro-1,2-diazin-3-on-4-yl, 4,5-dihydro-2H-pyridazin-3-on-4-yl, hexahydro-1,3-diazin-2,4-dion-5-yl, piperazin-2-on-3-yl, piperazin-2,6-dion-3-yl, tetrahydro-1,3,4-thiadiazin-5-on-6-yl, 5,6-dihydro-1,3,4-thiadiazin-5-on-6-yl, 1,3,4-oxadiazin-5-on-6-yl, 5,6-dihydro-1,2,4-oxadiazin-5-on-6-yl, tetrahydro-1,2,4-oxadiazin-5-on-6-yl, 1,2,4-triazin-5-on-6-yl, tetrahydro-1,2,4-oxadiazin-5-on-6-yl, 5,6-dihydro-1,2,4-oxadiazin-5-on-6-yl, 1,2,4-oxadiazin-3,5-dion-6-yl, or 1,2,4-triazin-6-on-5-yl;

Ar$^1$ and Z may be optionally substituted on any of the ring carbon atoms capable of forming an additional bond by one to three substituents independently selected from F, Cl, Br, CN, OH, (C$_1$–C$_4$)alkyl, (C$_1$–C$_4$)perfluoroalkyl, (C$_1$–C$_4$)perfluoroalkyloxy, (C$_1$–C$_4$)alkyloxy, and (C$_3$–C$_8$)cycloalkyloxy;

or a pharmaceutically acceptable salt thereof.

2. A compound according to claim 1, wherein R$^2$ and R$^3$ are each hydrogen.

3. A compound according to claim 2, wherein X is oxygen, —OCH$_2$— or —CH$_2$O—.

4. A compound according to claim 2, wherein X is sulfur, >SO$_2$, —SCH$_2$—, —CH$_2$S—, —CH$_2$SO$_2$— or —SO$_2$CH$_2$—.

5. A compound according to claim 2, wherein X is >NR$^4$, —CH$_2$N(R$^4$)— or —N(R$^4$)CH$_2$—.

6. A compound according to claim 2, wherein X is —N(R$^4$)SO$_2$— or —SO$_2$N(R$^4$)—.

7. A compound according to claim 2, wherein Y is a bond, oxygen, sulfur, —CH$_2$—, >SO$_2$, —OCH$_2$— or —CH$_2$O—.

8. A compound according to claim 3, wherein Y is a bond, oxygen, sulfur, —CH$_2$—, >S$_2$, —OCH$_2$— or —CH$_2$O—.

9. A compound according to claim 4, wherein Y is a bond, oxygen, sulfur, —CH$_2$—, >SO$_2$, —OCH$_2$— or —CH$_2$O—.

10. A compound according to claim 5, wherein Y is a bond, oxygen, sulfur, —CH$_2$, >SO$_2$, —OCH$_2$— or —CH$_2$O—.

11. A compound according to claim 6, wherein Y is a bond, oxygen, sulfur, —CH$_2$, >SO$_2$, —OCH$_2$— or —CH$_2$O—.

12. A compound according to claim 2, wherein Y is oxygen, —OCH$_2$— or —CH$_2$O—.

13. A compound according to claim 3, wherein Y is oxygen, —OCH$_2$— or —CH$_2$O—.

14. A compound according to claim 2, wherein X and Y are each oxygen.

15. A compound according to claim 2, wherein Ar$^1$ phenyl.

16. A compound according to claim 12, wherein Ar$^1$ is phenyl.

17. A compound according to claim 13, wherein Ar$^1$ is phenyl.

18. A compound according to claim 14, wherein Ar$^1$ is phenyl.

19. A compound according to claim 2, wherein Z is (C$_6$–C$_{10}$)aryl, pyridyl, furyl, pyrroyl, thienyl, isothiazolyl, imidazolyl, benzimidazolyl, tetrazolyl, pyrazinyl, pyrimidy, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

20. A compound according to claim 3, wherein Z is (C$_6$–C$_{10}$)aryl, pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

21. A compound according to claim 12, wherein Z is (C$_6$–C$_{10}$)aryl, pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

22. A compound according to claim 13, wherein Z is (C$_6$–C$_{10}$)aryl, pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

23. A compound according to claim 17, wherein Z is (C$_6$–C$_{10}$)aryl, pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

24. A compound according to claim 2, wherein Z is (C$_6$–C$_{10}$)aryl.

25. A compound according to claim 2, wherein Z is (C$_3$–C$_8$)cycloalkyl or (C$_3$–C$_8$)cycloalky(C$_1$–C$_4$)alkyl; wherein said (C$_3$–C$_8$)cycloalkyl moiety of said (C$_3$–C$_8$) cycloalkyl or (C$_3$–C$_8$)cycloalkyl(C$_1$–C$_4$)alkyl may optionally be replaced by tetrahydrofuranyl, tetrahydropyranyl, N-methyl-3-azetidinyl, piperazinyl, piperidinyl, 1,3-oxazolidin-4-on-5-yl, 1,3-oxazolidin-2,4-dion-5-yl, 4,5-dihydro-1,2-oxazolidin-3-on-4-yl, 1,3-thiazolidin-4-on-5-yl, 1,3-thiazolidin-2,4-dion-5-yl, 1,3-imidazolidin-4-on-5-yl, 1,3-imidazolidin-2,4-dion-5-yl, 1,2-pyrazolidin-3-on-4-yl, tetrahydro-1,3-oxazin-4-on-5-yl, tetrahydro-1,3-oxazin-2,4-dion-5-yl, morpholinyl, morpholin-3-on-2-yl, morpholin-3,5-dion-2-yl, 2,3-dihydro-1,4-oxazin-3-on-2-yl, tetrahydro-1,3-thiazin-4-on-5-yl, tetrahydro-1,3-thiazin-2,4-dion-5-yl, thiomorpholinyl, thiomorpholin-3-on-2-yl, thiomorpholin-3,5-dion-2-yl, 2,3-dihydro-1,4-thiazin-3-on-2-yl, hexahydro-1,2-diazin-3-on-4-yl, 4,5-dihydro-2H-pyridazin-3-on-4-yl, hexahydro-1,3-diazin-2,4-dion-5-yl, piperazin-2-on-3-yl, piperazin-2,6-dion-3-yl, tetrahydro-1,3,4-thiadiazin-5-on-6-yl, 5,6-dihydro-1,3,4-thiadiazin-5-on-6-yl, 1,3,4-oxadiazin-5-on-6-yl, 5,6-dihydro-1,2,4-oxadiazin-5-on-6-yl, tetrahydro-1,2,4-oxadiazin-5-on-6-yl, 1,2,4-triazin-5-on-6-yl, tetrahydro-1,2,4-oxadiazin-5-on-6-yl, 5,6-dihydro-1,2,4-oxadiazin-5-on-6-yl, 1,2,4-oxadiazin-3,5-dion-6-yl or 1,2,4-triazin-6-on-5-yl; optionally substituted on a nitrogen atom by $(C_1-C_4)$alkyl, $(C_6-C_{10})$aryl, pyridyl, furyl, pyrroyl, thienyl, isothiazolyl, imidazolyl, benzimidazolyl, tetrazolyl, pyrazinyl, pyrimidyl, quinolyl, isoquinoly, benzofuryl, isobenzofuryl, benzothienyl, pyrazolyl, indolyl, isoindolyl, purinyl, carbazolyl, isoxazolyl, thiazolyl, oxazolyl, benzthiazolyl, benzoxazolyl, OH, —$CONH_2$, —$CONHR^4$, —$CON(R^4)_2$ or $(C_3-C_8)$ cycloalkyl.

26. A compound according to claim 2, wherein Z is pyridyl, furyl, pyrroyl, thienyl, isothiazoly, imidazolyl, benzimidazolyl, tetrazolyl, pyrazinyl, pyrimidyl, quinolyl, isoquinoly, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

27. A compound according to claim 2, wherein $Ar^1$ and Z are substituted on any of the ring carbon atoms capable of forming an additional bond by one to three substituents independently selected from F, Cl, Br, CN, OH, $(C_1-C_4)$ alkyl, $(C_1-C_4)$perfluoroalkyl, $(C_1-C_4)$perfluoroalkyloxy, $(C_1-C_4)$alkyloxy and $(C_3-C_8)$cycloalkyloxy.

28. A compound according to claim 1 wherein X is oxygen, Y is a bond, oxygen, sulfur, —$CH_2$—>$SO_2$, —$OCH_2$— or —$CH_2O$—; $R^1$ is hydrogen or $(C_1-C_4)$alkyl, wherein said $(C_1-C_4)$alkyl may optionally contain one to two heteroatoms independently selected from oxygen and >$NR^5$, and wherein said $(C_1-C_4)$alkyl may optionally be substituted by one to three substituents independently selected from $(C_1-C_4)$alkyl, OH, $NH_2$, $(C_1-C_4)$alkylamino, di[$(C_1-C_4)$alkyl]amino, $(C_1-C_4)$alkyloxy, —$CONH_2$, —$CONHR^4$ and —$CONR^4$ and $R^2$ and $R^3$ are independently selected from hydrogen and $(C_1-C_4)$alkyl.

29. A compound according to claim 1, wherein $R^2$ and $R^3$ are each hydrogen; X is oxygen; Y is oxygen; and Z is pyridyl, furyl, pyrroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl.

30. A compound according to claim 1, wherein $R^1$ is methyl; $R^2$ and $R^3$ are each hydrogen; X is oxygen; Y is oxygen; and Z is $(C_6-C_{10})$aryl.

31. A compound according to claim 1, wherein $R^1$ is n-butyl; $R^2$ and $R^3$ are each hydrogen; X is oxygen; Y is oxygen; and Z is $(C_6-C_{10})$aryl.

32. A compound according to claim 1, wherein $R^1$ is methyl; $R^2$ and $R^3$ are each hydrogen; X is oxygen; Y is a bond; and Z is $(C_6-C_{10})$aryl.

33. A compound according to claim 1, wherein $R^1$ is n-butyl; $R^2$ and $R^3$ are each hydrogen; X is oxygen; Y is a bond; and Z is $(C_6-C_{10})$aryl.

34. A compound according to claim 1, wherein said compound is selected from the group consisting of:

5-Methyl-5-(4-phenoxy-phenoxy)-pyrimidine-2,4,6-trione;

5-Methyl-5-(4-(4'-fluorophenoxy)-phenoxy)-pyrimidine-2,4,6-trione;

5-n-Butyl-5-(4-phenoxy-phenoxy)-pyrimidine-2,4,6-trione;

5-n-Butyl-5-(4-(4'-fluorophenoxy)-phenoxy)-pyrimidine-2,4,6-trione;

5-Methyl-5-(4-phenyl-phenoxy)-pyrimidine-2,4,6-trione;

5-Methyl-5-(3-phenyl-phenoxy)-pyrimidine-2,4,6-trione; and

5-Methyl-5-(4-benzyloxy-phenoxy)-pyrimidine-2,4,6-trione;

or a pharmaceutically acceptable salt thereof.

* * * * *